(12) United States Patent
Schmidt et al.

(10) Patent No.: US 8,712,500 B2
(45) Date of Patent: Apr. 29, 2014

(54) IMAGE-MONITORING METHOD FOR ELECTROPORATION TREATMENT AND AS ASSOCIATED IMAGE-MONITORING APPLIANCE

(75) Inventors: Sebastian Schmidt, Weisendorf (DE); Anke Weissenborn, Weil am Rhein (DE)

(73) Assignee: Siemens Aktiengesellschaft, Munich (DE)

(*) Notice: Subject to any disclaimer, the term of this patent is extended or adjusted under 35 U.S.C. 154(b) by 372 days.

(21) Appl. No.: 12/897,984

(22) Filed: Oct. 5, 2010

(65) Prior Publication Data
US 2011/0082362 A1 Apr. 7, 2011

(30) Foreign Application Priority Data
Oct. 5, 2009 (DE) .................. 10 2009 048 264

(51) Int. Cl.
*A61B 5/055* (2006.01)
(52) U.S. Cl.
USPC ............ 600/411; 600/407; 600/427; 600/431
(58) Field of Classification Search
USPC .......................................... 600/411, 427, 431
See application file for complete search history.

(56) References Cited

U.S. PATENT DOCUMENTS

| 6,272,370 | B1* | 8/2001 | Gillies et al. ................. 600/411 |
| 6,575,969 | B1* | 6/2003 | Rittman et al. ................. 606/41 |
| 2001/0037062 | A1* | 11/2001 | Ehnholm ....................... 600/414 |
| 2003/0050557 | A1* | 3/2003 | Susil et al. ..................... 600/424 |
| 2004/0044281 | A1* | 3/2004 | Jesberger et al. ............. 600/419 |
| 2006/0264752 | A1* | 11/2006 | Rubinsky et al. ............. 600/439 |
| 2007/0020326 | A1 | 1/2007 | Walker et al. |
| 2007/0123815 | A1* | 5/2007 | Mark .............................. 604/22 |
| 2009/0024075 | A1 | 1/2009 | Schroeppel et al. |

FOREIGN PATENT DOCUMENTS

DE 102008030242 A1 1/2010

OTHER PUBLICATIONS

Thomas J. Vogl et al.: Prostate Cancer: MR Imaging guided Galvanotherapy—Technical Development and First Clinical Results; Radiology: vol. 245: No. 3, Dec. 2007.
Boris Rubinsky et al.: Irreversible Electroporation: A New Ablation Modality—Clinical Implications; Technology in Cancer Research and Treatment, Feb. 2007; vol. 6, No. 1; pp. 37-48.
Garcia et al., "Pilot Study of Irreversible Electroporation for Intracranial Surgery", 31st Annual International Conference of the IEEE EMBS, Minneapolis, Minnesota, USA, Sep. 2-6, 2009, pp. 6513-6516.

* cited by examiner

*Primary Examiner* — Jonathan Cwern

(57) ABSTRACT

An image-monitoring method for an electroporation treatment with an electroporation appliance is provided. The electroporation appliance comprises at least two treatment electrodes and an image-monitoring appliance. At least one image monitoring measurement is performed by the image-monitoring appliance after the administration of a contrast agent and after the electroporation treatment.

17 Claims, 2 Drawing Sheets

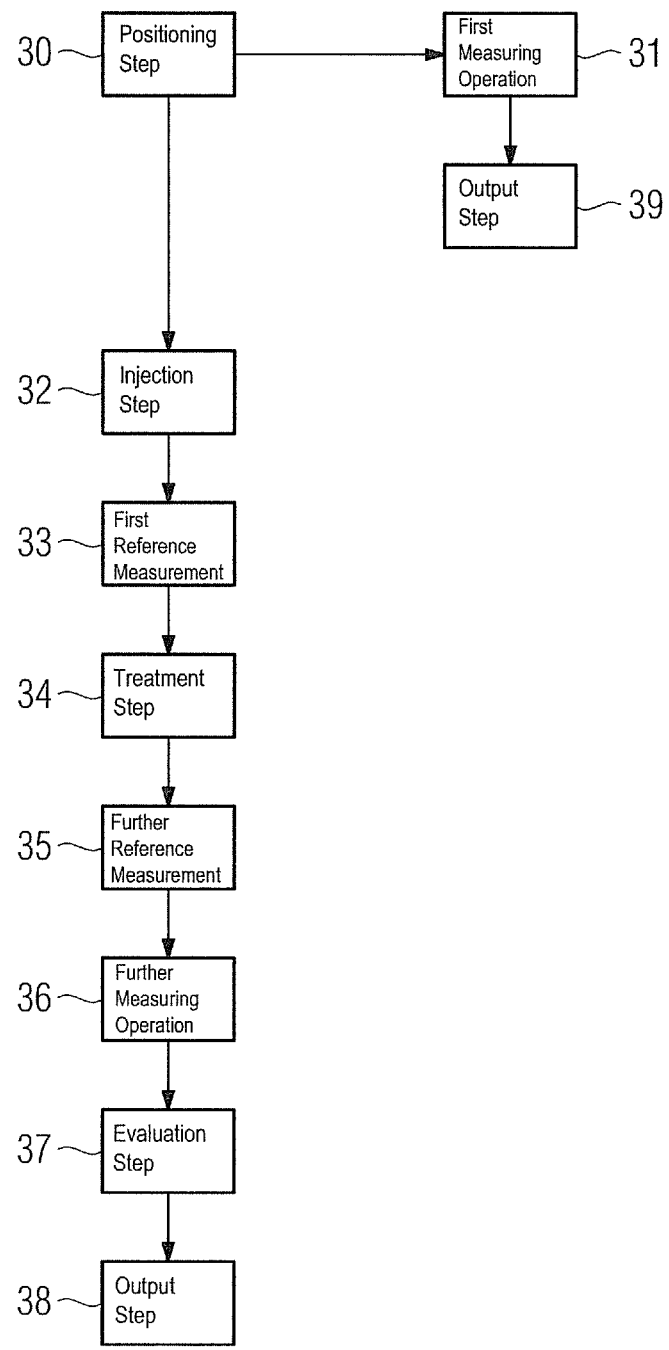

IMAGE-MONITORING METHOD FOR ELECTROPORATION TREATMENT AND AS ASSOCIATED IMAGE-MONITORING APPLIANCE

CROSS REFERENCE TO RELATED APPLICATIONS

This application claims priority of German application No. 10 2009 048 264.4 filed Oct. 5, 2009, which is incorporated by reference herein in its entirety.

FIELD OF THE INVENTION

The invention is based on an image-monitoring method for electroporation treatment and an associated image-monitoring appliance.

BACKGROUND OF THE INVENTION

Electroporation is a method for damaging tumors in such a way that their growth is retarded or they are destroyed. To this end, electrodes are introduced into a patient's tissue via which high electrical voltages in a range of more than 1000 V are applied over a short period, preferably in a range of microseconds to a maximum of a few milliseconds. Electroporation causes an increase in the permeability of the cell membrane through which substances are subsequently able to enter or exit the cell. This effect is used, for example, in cancer therapy in conjunction with the administration of chemotherapy agents in order to introduce the chemotherapy agent selectively into the cells, in particular into tumor cells. The application of stronger electric fields causes defects to form in the cells; these defects are irreversible and ultimately result in the death of the cell since the cell loses its self-regulatory mechanisms—this effect is, therefore, primarily used for the treatment of tumors.

For electroporation treatment, at least two treatment electrodes are introduced into a body to be treated, wherein the treatment electrodes come into contact with a region of the body to be treated, such as, for example, a tumor. The treatment electrodes are generally used to generate bipolar electroporation pulses, which in particular have a voltage in the range of a few KV and are applied with a time interval of approximately one second about 10 times, see in this context "Irreversible Electroporation: A New Ablation Modality—Clinical Implications" by Boris Rubinsky, Technology in Cancer Research and Treatment, Vol. 6, 2007, pages 37-48.

Known for monitoring and/or verification of irreversible electroporation treatment is an ultrasound measuring appliance for determining and/or monitoring the positioning of the treatment electrodes. However, this type of monitoring only determines an effect of electroporation weakly and with a delay. In addition, the monitoring requires activity on the part of the patient to be treated.

SUMMARY OF THE INVENTION

The object underlying the invention is to disclose a method with efficient and high-speed image monitoring for verification of electroporation treatment.

The invention is based on an image-monitoring method for electroporation treatment with an electroporation appliance comprising at least two treatment electrodes and an image-monitoring appliance.

It is proposed that at least one image monitoring measurement be performed by means of the image-monitoring appliance after the administration of a contrast agent and after electroporation treatment. The electroporation treatment causes, at least temporarily, the permeability of a cell wall to increase so that the contrast agent is able to enter an intracellular space. Preferably, an image monitoring measurement is performed by measuring and/or determining the relative concentration of the contrast agent in the intracellular space in comparison to the contrast agent concentration in the extracellular space, wherein the contrast agent is exclusively provided for the intensification of a selective representation of different tissue sections. The contrast agent advantageously intensifies a magnetic resonance effect for a magnetic resonance measurement so that areas with a high contrast agent concentration can be differentiated from areas with a low contrast agent concentration by means of a magnetic resonance imaging measurement. The embodiment according to the invention advantageously enables efficient and high-speed image monitoring for verification of the electroporation treatment, such as, for example, tumor treatment. In addition, it is possible on the basis of the image-monitoring method to produce a diagnosis of the outcome of the electroporation treatment particularly quickly, since a maximum concentration of the contrast agent within the cells is achieved shortly after the electroporation treatment because the molecules of the contrast agent are able to diffuse through the cell wall into the interior of the cell due to the high permeability of the cell wall.

In addition, it is proposed that, by means of the image-monitoring appliance embodied as a magnetic resonance appliance or as a computed tomography appliance, at least one magnetic resonance image or at least one computed tomography image is recorded during the image monitoring measurement. Magnetic resonance imaging methods or a computed tomography methods are particularly advantageously suitable for monitoring electroporation treatments since it is also advantageously possible to use a conventional contrast agent such as those used with a magnetic resonance imaging method or a computed tomography method with electroporation treatment due to the low molecular size of the contrast agent. In addition, the magnetic resonance imaging method is in particular suitable for a verification of the electroporation method, since an electroporation method is performed with d.c. pulses and is hence compatible with magnetic resonance imaging. Hereby, it is also of advantage, for the electroporation appliance to comprise treatment electrodes compatible with magnetic resonance imaging. The use of treatment electrodes compatible with magnetic resonance imaging and also the performance of the treatment itself do not cause any interference to the magnetic resonance images so that the monitoring can take place with high image quality. On the other hand, an interfering, and in particular unwanted, influence of a high magnetic resonance imaging field on the effectiveness of the treatment can be advantageously prevented so that radioactive contamination of patients and/or people performing the treatment can be avoided.

Particularly advantageously, an area affected by the electroporation treatment is determined in an evaluation step by means of a measured intracellular concentration of the contrast agent in that the contrast agent is able to enter the cell immediately after the electroporation treatment and, due to an at least partially occurring self-healing effect with which the defects occurring in the cell membrane are closed by regeneration of the cell membrane, is at least partially trapped in the cell. While the concentration of the contrast agent in the extracellular space is slowly eliminated, the concentration of the contrast agent in the cell remains approximately constant. Therefore, the intracellular concentration can be determined in relation to an extracellular concentration and/or absolutely by means of an analysis of a measured signal strength.

If a treatment step for the electroporation treatment is performed after the administration of the contrast agent, the electroporation treatment can take place with a high contrast agent concentration in the extracellular space and hence the contrast agent can penetrate the cell after the electroporation treatment. Hence, the regeneration of the cells before the entrance of the contrast agent in the cells can be advantageously prevented.

It is also proposed that a treatment step for the electroporation treatment be performed with a substantially maximum concentration of the contrast agent in the extracellular space which enables a maximum intracellular contrast agent concentration to be achieved. In addition, in association with this, it is possible to achieve a maximum difference at a later measuring time in the concentration between the intracellular and the extracellular space. For a typical contrast agent, such as, for example, a gadolinium-based contrast agent, the maximum concentration of the contrast agent in the extracellular space is achieved approximately 60 to 100 seconds after an injection of the contrast agent so that advantageously the contrast agent is administered intravenously in an injection step approximately 100 to 200 seconds before the electroporation treatment.

In an advantageous development of the invention, it is proposed that the at least one image monitoring measurement be performed substantially after the duration of at least one half-life period of the contrast agent after the administration of the contrast agent. In this context, a half-life period should be in particular understood as meaning that the concentration of the contrast agent in the extracellular space after the duration of the half-life period is approximately 50% eliminated from the extracellular space. For example, the half-life period for a gadolinium-chelate contrast agent is typically approximately 2 hours. Hereby, it is possible to measure an advantageous contrast agent concentration difference between the intracellular and extracellular space by means of the image-monitoring appliance and hence, in association with this, advantageously to determine the outcome of the electroporation treatment. In the case of contrast agents with long half-life periods, this is in particular of advantage in order to obtain high-speed image monitoring of the electroporation treatment.

A particularly advantageous concentration difference between the intracellular and extracellular space can be achieved if the at least one image monitoring measurement is performed substantially after the duration of at least two half-life periods of the contrast agent after the administration of the contrast agent.

It is also proposed that at least two image-monitoring measurements be performed at different times after the administration of the contrast agent thus enabling a course, in particular a decrease, of the contrast agent concentration over time in areas affected by the electroporation treatment and/or in areas protected from the electroporation treatment to be displayed. Alternatively or additionally, continuous image monitoring measurement, in particular by means of the magnetic resonance appliance with magnetic resonance images, is possible.

It is also proposed that an extracellular contrast agent with a small molecular size is used, thus making it easier for the contrast agent to penetrate the cells immediately after the electroporation treatment. Hereby, an extracellular contrast agent should in particular be understood to mean a contrast agent which is unable to penetrate the cell membrane of healthy cells and the therefore remains in the extracellular space. Preferably, in the case of an image monitoring measurement formed from a magnetic resonance measurement, the contrast agent is formed from a gadolinium-based contrast agent. In addition, contrast agents based on fluorine and/or based on hyperpolarized substances, such as, for example, $^{13}C$, $^{15}N$ and/or contrast agents based on principles such as CEST (chemical exchange dependant saturation transfer) are also advantageous. If the image monitoring measurement is formed from a computed tomography measurement, a contrast agent embodied as a conventional X-ray contrast agent based on iodine-compounds is particularly suitable.

It is also proposed that at least one reference measurement be performed before the treatment step for the electroporation treatment, thus enabling an effect of the electroporation treatment to be displayed particularly selectively. Alternatively or additionally, at least one reference measurement can be performed after the administration of the contrast agent. Hereby, it is possible in particular to achieve a particularly effective contrast intensification in the affected area by means of the image-monitoring appliance in that, in at least one evaluation step, the at least one reference measurement is at least partially subtracted from the image monitoring measurement.

Particularly advantageously, in at least one measuring operation, an image monitoring measurement is recorded parallel to a positioning step for the positioning of the treatment electrodes thus enabling the achievement of an exact positioning of the treatment electrodes, in particular in and/or on a tumor. Preferably, to this end, at least partial regions of the electroporation appliance, in particular the treatment electrodes and/or means for introducing and/or positioning the treatment electrodes, are formed from non-magnetic materials.

In addition, the invention is based on an image-monitoring appliance for an image-monitoring method for electroporation treatment, wherein the image-monitoring appliance comprises an electroporation appliance with at least two treatment electrodes.

It is proposed that the image-monitoring appliance comprises a magnetic resonance appliance or a computed tomography appliance provided for image monitoring by means of a contrast agent. Magnetic resonance imaging methods or computed tomography methods are particularly advantageously suitable for monitoring electroporation treatments, since a conventional contrast agent used with a magnetic resonance imaging method or a computed tomography method can also be advantageously used with electroporation treatment due to the low molecular size of the contrast agent.

It is also proposed that the at least two treatment electrodes are compatible with magnetic resonance imaging. The use of treatment electrodes compatible with magnetic resonance imaging and also the performance of the treatment itself mean that there is no interference to the magnetic resonance images so that the monitoring can take place with high image quality. On the other hand, an interfering, and in particular unwanted, influence of a high magnetic resonance imaging field on the effectiveness of the treatment can be advantageously prevented so that radioactive contamination of patients and/or people performing the treatment can be avoided. Preferably, the treatment electrodes are embodied as needle electrodes which can be placed on the patient by means of a positioning unit and moved into a prespecified position. The electroporation appliance comprises preferably two or four treatment electrodes, wherein, in an alternative embodiment of the invention, additional treatment electrodes are always conceivable.

It is also proposed that the magnetic resonance appliance or the computed tomography appliance comprises a control unit provided for at least partial control of the electroporation appliance. It is possible to achieve direct, and in particular mutually adapted, control of the electroporation appliance and the magnetic resonance appliance or the computed tomography appliance advantageously saving further components and costs. To this end, the magnetic resonance appliance is particularly suitable for controlling the electroporation appliance, in particular for the generation of electroporation pulse sequences, since this is already designed to generate and process pulse sequences for gradient coils and high-frequency coils. The gradient coils are hereby controlled by the channels of a gradient amplifier assigned to the gradient coils and the treatment electrodes can be controlled via an additional gradient amplifier channel by the control unit.

Particularly advantageously, the image-monitoring appliance comprises a contrast agent unit provided for the administration of the contrast agent. Preferably, the administration takes place by means of an injection of the contrast agent. The administration, in particular the injection, of the contrast agent can in particular be adapted to a temporal course of the image monitoring measurement and/or the electroporation treatment. Preferably, the administration of the contrast agent takes place at least partially automatically by means of the contrast agent unit.

Preferably, the contrast agent unit comprises an injection needle which is compatible with magnetic resonance imaging so that unwanted interference of an injection process and/or the image monitoring measurement, in particular of magnetic resonance measurements, can be avoided and the monitoring can take place with high image quality. In addition, an interfering, and in particular unwanted, influence of a high magnetic resonance imaging field on the injection process can be advantageously avoided so that radioactive contamination of patients and/or people performing the treatment can be avoided.

In an advantageous development of the invention, it is proposed that the magnetic resonance appliance or the computed tomography appliance comprises a control unit provided for at least partial control of the contrast agent unit. It is possible to achieve direct, and in particular mutually adapted control, of the contrast agent unit and the magnetic resonance appliance or the computed tomography appliance advantageously saving further components and costs.

BRIEF DESCRIPTION OF THE DRAWINGS

Further advantages and details of the present invention may be derived from the exemplary embodiments described below and with reference to the drawings which show.

DETAILED DESCRIPTION OF THE INVENTION

Figure 1:
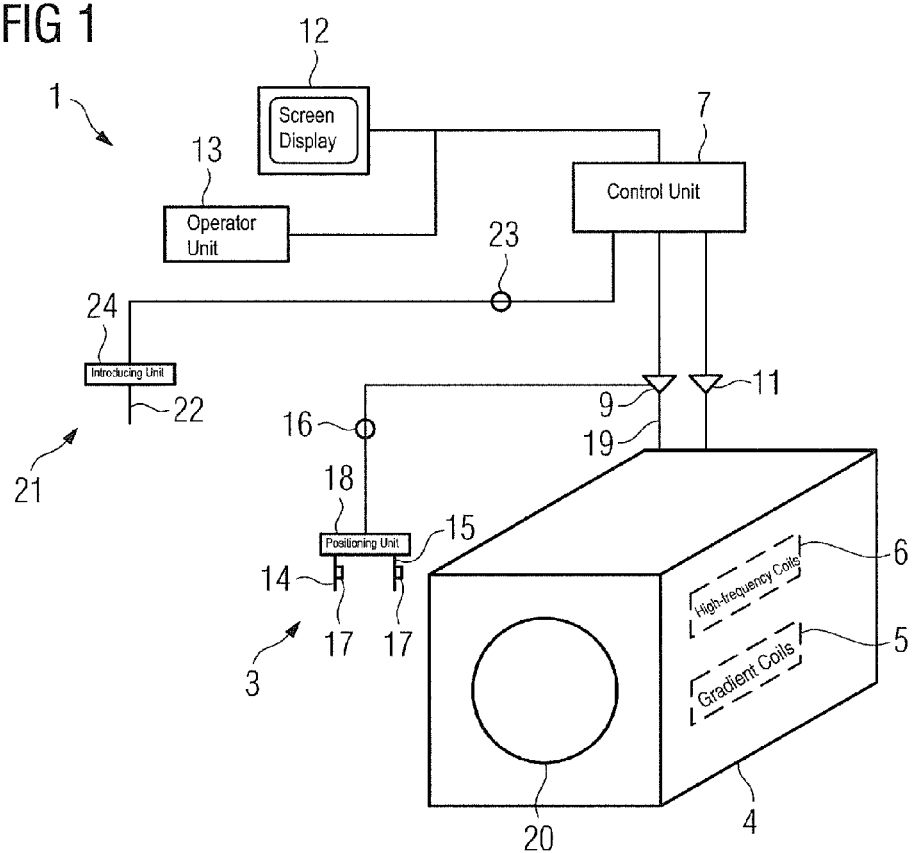
FIG. 1 an image-monitoring appliance according to the invention with a magnetic resonance appliance in a schematic representation, FIG. 2 an image-monitoring appliance according to the invention with a computed tomography appliance in a schematic representation and FIG. 3 a flowchart of an image-monitoring method according to the invention.

FIG. 1 shows an image-monitoring appliance 1 according to the invention for electroporation treatment. The image-monitoring appliance 1 comprises a magnetic resonance appliance 2, an electroporation appliance 3 and a contrast agent unit 21 formed from an injection unit. The magnetic resonance appliance 2 comprises a magnet 4 to generate a strong and constant magnetic field. In addition, the magnetic resonance appliance 2 comprises gradient coils 5 provided to generate a linear gradient field and high-frequency coils 6. The gradient coils 5 are controlled by a control unit 7 of the magnetic resonance appliance 2 via a gradient amplifier 9. The high-frequency coils 6 are controlled by the control unit 7 via a high-frequency amplifier 11. The magnetic resonance appliance 2 also comprises a screen display 12 by means of which magnetic resonance images and/or results evaluated by the control unit 7 can be displayed and an operator unit 13 by means of which an operator can make settings and/or parameter changes.

The electroporation appliance 3 provided for the performance of electroporation treatment comprises two treatment electrodes 14, 15 both formed from a needle electrode. In addition, the two treatment electrodes 14, 15 are made of a material compatible with magnetic resonance imaging in order to avoid interference during a magnetic resonance measurement. The electroporation appliance 3 is controlled via the control unit 7 of the magnetic resonance appliance 2 and can therefore also be operated via the operator unit 13. To this end, the control unit 7 of the magnetic resonance appliance 2 is also embodied as a sequencer for the electroporation appliance 3 and provided for the generation of electroporation pulse sequence when operational. The treatment electrodes 14, 15 are controlled by means of the gradient amplifier 9. Consequently, the control unit 7 is also embodied for processing electroporation pulse sequences and the gradient amplifier 9 comprises an additional channel to control the two treatment electrodes 14, 15.

The electroporation appliance 3 is also detachably connected to the magnetic resonance appliance 2 by connectors 16 so that, if required, it can be temporarily removed from the magnetic resonance appliance 2. In addition, the two treatment electrodes 14, 15 are provided with magnetic resonance markers 17 facilitating the unequivocal detectability of the two treatment electrodes 14, 15 in magnetic resonance images. Alternatively to this, an embodiment of the two treatment electrodes 14, 15 without magnetic resonance imaging markers 17 is also conceivable. For targeted positioning of the two treatment electrodes 14, 15, the electroporation appliance 3 comprises a positioning unit 18 which is also made of a non-magnetic material. The positioning unit 18 can be used to position the two treatment electrodes 14, 15 precisely on a location to be treated in a patient, such as, for example, on and/or in a tumor.

The injection unit is provided for the injection of a contrast agent and comprises an injection needle 22 which is compatible with magnetic resonance imaging. The injection unit is controlled by means of the control unit 7 of the magnetic resonance appliance 2. To this end, the control unit 7 generates control signals for the injection unit. The injection unit also comprises an introducing unit 24 which is also made of a non-magnetic material. The introducing unit 24 enables the injection needle 22 to be positioned precisely on a location in a patient. Similarly to the embodiment of the electroporation appliance 3, the injection unit is also connected detachably to the magnetic resonance appliance 2 via a connector 23 so that, if required, it can be removed temporarily from the magnetic resonance appliance 2.

The control unit 7 is connected to the individual components and units of the image-monitoring appliance 1 via a connection line 19 over which data and/or control signals can be exchanged when the image-monitoring appliance 1 is operational.

Alternatively, to this end, it is also always conceivable for the electroporation appliance 3 and/or the injection unit to be controlled separately from the magnetic resonance appliance 2, wherein, to this end, the electroporation appliance 3 and/or the injection unit are provided with a control unit which is independent of the magnetic resonance appliance 2.

In addition, the magnetic resonance appliance 2 comprises a receiving area 20 provided to receive a patient for a magnetic resonance measurement. Hereby, the patient is introduced by means of a patient bed (not shown in any more detail) at least partially into the receiving area 20 before the commencement of a magnetic resonance measurement.

FIG. 3 is a flowchart of an image-monitoring method according to the invention for the image-monitoring appliance 1. When the image-monitoring appliance 1 is operational, after the introduction of the patient into the receiving area 20 of the magnetic resonance appliance 2, in the image processing method, first a positioning step 30 is started in which treatment electrodes 14, 15 are placed on the patient by means of the positioning unit 18. Then, the two treatment electrodes 14, 15 are positioned in and/or on the tissue to be examined, such as, for example, in and/or on a tumor. Simultaneously, the magnetic resonance appliance 2 effects a first measuring operation 31 in which an image monitoring measurement is performed in parallel to the positioning of the two treatment electrodes 14, 15 and during this magnetic resonance images are recorded so that the two treatment electrodes 14, 15 can be positioned as precisely as possible by means of image monitoring. In an output step 39, the magnetic resonance images are forwarded by the control unit 7 to the screen display 12 and output there for a person operating the image-monitoring appliance 1. Simultaneously, the operator unit 13 may be used by the person operating the image-monitoring appliance 1 to change settings and/or parameters for the positioning of the two treatment electrodes 14, 15 in the positioning step 30.

Next, in an injection step 32, the patient is injected intravenously with a contrast agent by means of the injection unit. To this end, using the introducing unit 24 and controlled by the control unit 7, the injection needle 22 is brought to an injection position in and/or on the patient and the contrast agent injected. Similarly to the positioning step 30, the injection step 32 can also be monitored by means of the magnetic resonance appliance by recording magnetic resonance images in a measuring operation. In addition, the operator unit 13 can be used by the person operating the image-monitoring appliance 1 to change settings and/or parameters for the injection and/or to position the injection needle 22 in the injection step 32.

The contrast agent is formed from a gadolinium-based contrast agent with a small molecular size. Approximately 60 to 100 seconds after the injection, this contrast agent achieves its substantially maximum extracellular concentration.

After the administration of the contrast agent and still before the electroporation treatment, a first reference measurement 33 is performed by means of the magnetic resonance appliance 2 by recording magnetic resonance images, wherein the reference measurement 33 substantially reflects a concentration of the contrast agent in the extracellular space before commencing the electroporation treatment.

Approximately 100 to 200 seconds after the administration of the contrast agent, the electroporation treatment is started in a treatment step 34 so that at least temporary damage is caused to a cell wall by the electroporation treatment with a substantially maximum extracellular concentration of the contrast agent. Hereby, the control unit 7 generates an electroporation pulse sequence which is applied to the two treatment electrodes 14, 15 by means of the gradient amplifier 9. Due to the high pulses, the cell wall of the cells between the two treatment electrodes 14, 15 and/or in the vicinity of the two treatment electrodes 14, 15 is damaged at least temporarily.

Immediately after the electroporation treatment, a further reference measurement 35 is also performed by means of the magnetic resonance appliance 2 by recording magnetic resonance images, wherein the reference measurement 35 substantially reflects a concentration of the contrast agent in the intracellular and extracellular space a short time after the electroporation treatment.

Extracellular contrast agent is slowly eliminated from the patient's body, wherein a half-life period of the contrast agent represents a measure of the elimination of the contrast agent. After an at least partial elimination of the extracellular contrast agent, the image monitoring measurement by means of the magnetic resonance appliance 2 starts by recording magnetic resonance images in a further measuring operation 36. In order to achieve the greatest possible contrast in the contrast agent concentration between the intracellular and the extracellular cell space, at least one image monitoring measurement by means of the magnetic resonance appliance 2 is performed by recording magnetic resonance images after the duration of at least two half-life periods of the contrast agent after the administration of the contrast agent. A typical half-life period for the elimination of the contrast agent from the human body for a gadolinium-based contrast agent is approximately 2 hours. In the case of a contrast agent with a higher half-life period than a gadolinium-based contrast agent, it is also sufficient for the image monitoring measurement to be performed substantially after the duration of at least one half-life period of the contrast agent after the administration of the contrast agent so that a more rapid verification of the outcome of the electroporation treatment is achieved.

In addition, in the further measuring operation 36, at different times after the electroporation treatment, image-monitoring measurements by means of the magnetic resonance appliance 2 may be performed by recording magnetic resonance images. This enables the temporal course of the contrast agent concentration in area affected by the electroporation and in areas protected from the electroporation. Alternatively, in the further measuring operation 36, continuous image monitoring measurement by means of the magnetic resonance appliance 2 can take place over a coherent time interval and hence an uninterrupted temporal course of the contrast agent concentration in the time interval determined.

Then, in an evaluation step 37, the control unit 7 determines the intracellular contrast agent concentration and hence, in association with this, detects an area affected by the electroporation treatment and/or the success and/or verification of the electroporation treatment. Hereby, firstly a relative intracellular contrast agent concentration is determined from the magnetic resonance images, wherein the intracellular contrast agent concentration is determined in relation to an extracellular contrast agent concentration. For a particularly selective representation of the relative contrast agent concentration and hence the effect of the electroporation treatment, in the evaluation step 37, data in the magnetic resonance images of the reference measurements are subtracted from the data in the magnetic resonance images of the image monitoring measurements so that a contrast agent difference between the intracellular and the extracellular space in the area and/or areas covered by the electroporation is intensified and a high contrast is achieved in an output image generated for an output by means of the screen display 12 for differentiation of the different areas.

In addition, in the evaluation step 37, the control unit 7 determines an absolute concentration of the contrast agent in the intracellular space. To this end, signal strengths of the magnetic resonance images of the image monitoring measurements are evaluated, wherein the signal strength represents a measure for the contrast agent concentration and hence the absolute concentration of the contrast agent in intracellular space is determined.

Then, the data evaluated by the control unit 7 is output and/or displayed in an output step 38 by the screen display 12 for the staff operating the image-monitoring appliance 1. To this end, the control unit 7 generates output images showing the contrast agent concentration in relation to a measured location. Hereby, in addition to the relative intracellular contrast agent concentration, it is also possible to display the absolute contrast agent concentration. In addition, it is possible to display a course of the contrast agent concentration graphically as a curve and/or a course of the contrast agent concentration over time in areas affected by the electroporation treatment and areas protected from the electroporation treatment. Hereby, the staff operating the image-monitoring appliance 1 can use the operator unit 13 together with the screen display 12 to select a display variant for the contrast agent concentration.

In a further embodiment of the invention, it can also be provided that, together with the contrast agent, a therapeutic substance, in particular a chemotherapeutic agent such as, for example, bleomycin, is injected. Hereby, the uptake of the contrast agent in the cells affected by the electroporation treatment represents a measure for the uptake of the therapeutic substance in the cells so that in this way chemotherapy treatment can be verified and/or monitored.

Figure 2:
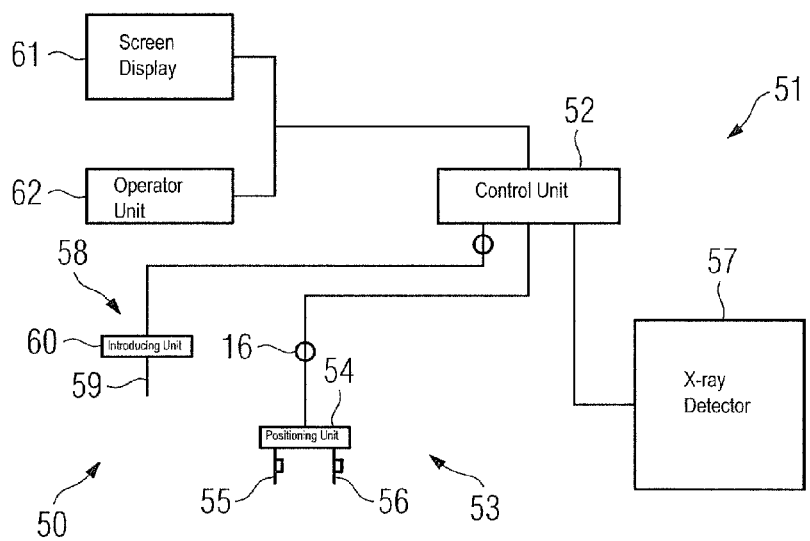

FIG. 2 shows an alternative design of the image-monitoring appliance 50 to that shown in FIG. 1. The image-monitoring appliance 50 differs from the image-monitoring appliance 1 shown in FIG. 1 in that, instead of the magnetic resonance appliance 2, a computed tomography appliance 51 is used. The computed tomography appliance 51 records computed tomography images for image monitoring measurements and/or reference measurements. The image-monitoring appliance 50 also comprises an electroporation appliance 53 and a contrast agent unit 58.

The computed tomography appliance 51 comprises a control unit 52 provided to control an X-ray detector 57, the electroporation appliance 53 and the contrast agent unit 58. Hereby, the control unit 52 is also provided for the generation of electroporation pulse sequences. The electroporation appliance 53 comprises a positioning unit 54 and two treatment electrodes 55, 56 compatible with magnetic resonance imaging. The contrast agent unit 58 comprises an introducing unit 60 and an injection needle 59 compatible with magnetic resonance imaging, wherein the contrast agent unit 58 is also controlled by the control unit 52.

In addition, the computed tomography appliance 51 comprises a screen display 61, by means of which computed tomography images and/or results evaluated by the control unit 52 can be displayed and an operator unit 62, by means of which an operator can make settings and/or parameter changes.

The mode of operation of an image-monitoring method for the image-monitoring appliance 50 shown in FIG. 2 corresponds to the explanations of the image-monitoring method for FIG. 3, wherein instead of a gadolinium-based contrast agent, a conventional computed tomography contrast agent based on iodine compounds is used.

The invention claimed is:

1. An image-monitoring method for an electroporation treatment, comprising:
    administrating a contrast agent into a patient;
    performing the electroporation treatment by an electroporation appliance comprising a plurality of treatment electrodes after administrating the contrast agent;
    performing a reference measurement by an image recording appliance immediately after the electroporation treatment;
    performing a continuous image monitoring measurement by the image recording appliance over a time interval after the electroporation treatment;
    determining a relative intracellular contrast agent concentration in comparison to an extracellular contrast agent concentration from the image monitoring measurement;
    determining an absolute intracellular contrast agent concentration from the image monitoring measurement;
    generating an output image showing a course of contrast agent concentration over the time interval by subtracting data in the reference measurement from data in the image monitoring measurement so that a contrast agent difference between an intracellular and an extracellular space in an area affected by the electroporation treatment is intensified; and
    displaying the relative and the absolute intracellular contrast agent concentration and the output image on a screen display.

2. The image-monitoring method as claimed in claim 1, wherein the image recording appliance comprises a magnetic resonance appliance for recording a magnetic resonance image or a computed tomography appliance for recording a computed tomography image during the image monitoring measurement.

3. The image-monitoring method as claimed in claim 1, wherein the area affected by the electroporation treatment is determined based on the relative intracellular contrast agent concentration.

4. The image-monitoring method as claimed in claim 1, wherein the electroporation treatment is performed after the administration of the contrast agent.

5. The image-monitoring method as claimed in claim 1, wherein the electroporation treatment is performed with a substantially maximum concentration of the contrast agent in the extracellular space.

6. The image-monitoring method as claimed in claim 1, wherein the image monitoring measurement is performed substantially after a duration of one half-life period of the contrast agent after administrating the contrast agent.

7. The image-monitoring method as claimed in claim 1, wherein the image monitoring measurement is performed substantially after a duration of two half-life periods of the contrast agent after administrating the contrast agent.

8. The image-monitoring method as claimed in claim 1, wherein the continuous image monitoring measurement is performed at different times over the time interval.

9. The image-monitoring method as claimed in claim 1, wherein the contrast agent comprises an extracellular contrast agent with a small molecular size.

10. The image-monitoring method as claimed in claim 1, wherein a first reference measurement is performed before performing the reference measurement, wherein the first reference measurement is performed after administrating the contrast agent and before the electroporation treatment, and wherein data in the first or in the reference measurement is partially subtracted from data in the image monitoring measurement.

11. The image-monitoring method as claimed in claim 1, wherein a first image monitoring measurement is performed before performing the continuous image monitoring measurement by the image recording appliance for positioning the treatment electrodes.

12. An image-monitoring appliance for an electroporation treatment, comprising:
   a contrast agent unit for administrating a contrast agent into a patient;
   an electroporation appliance comprising a plurality of treatment electrodes for performing the electroporation treatment;
   an image recording appliance for performing:
      a reference measurement immediately after the electroporation treatment, and
      a continuous image monitoring measurement over a time interval after administrating the contrast agent and after the electroporation treatment; and
   a control unit for:
      determining a relative intracellular contrast agent concentration in comparison to an extracellular contrast agent concentration from the image monitoring measurement;
      determining an absolute intracellular contrast agent concentration from the image monitoring measurement
      generating an output image showing a course of contrast agent concentration over the time interval by subtracting data in the reference measurement from data in the image monitoring measurement so that a contrast agent difference between an intracellular and an extracellular space in an area affected by the electroporation treatment is intensified; and
   a screen display for displaying the relative and the absolute intracellular contrast agent concentration and the output image.

13. The image-monitoring appliance as claimed in claim 12, wherein the image recording appliance comprises a magnetic resonance appliance or a computed tomography appliance.

14. The image-monitoring appliance as claimed in claim 12, wherein the control unit is adapted to partially control the electroporation appliance.

15. The image-monitoring appliance as claimed in claim 12, wherein the control unit is adapted to partially control the contrast agent unit.

16. The image-monitoring appliance as claimed in claim 12, wherein the contrast agent unit comprises an injection needle compatible with magnetic resonance imaging.

17. The image-monitoring appliance as claimed in claim 12, wherein the treatment electrodes are compatible with magnetic resonance imaging.

* * * * *